United States Patent
Kawasaki et al.

(10) Patent No.: US 12,194,185 B2
(45) Date of Patent: Jan. 14, 2025

(54) CONTINUOUS DECONTAMINATION DEVICE

(71) Applicant: AIREX CO., LTD., Aichi (JP)

(72) Inventors: Koji Kawasaki, Aichi (JP); Daisuke Kakuda, Aichi (JP); Jun Masudome, Aichi (JP); Haruka Futamura, Aichi (JP); Yukihiro Yazaki, Aichi (JP); Tsukasa Kitano, Aichi (JP); Zhiqiang Guo, Aichi (JP); Ayumi Ogawa, Aichi (JP)

(73) Assignee: AIREX CO., LTD., Aichi (JP)

( * ) Notice: Subject to any disclaimer, the term of this patent is extended or adjusted under 35 U.S.C. 154(b) by 705 days.

(21) Appl. No.: 17/599,699

(22) PCT Filed: Mar. 17, 2020

(86) PCT No.: PCT/JP2020/011721
§ 371 (c)(1),
(2) Date: Sep. 29, 2021

(87) PCT Pub. No.: WO2020/203257
PCT Pub. Date: Oct. 8, 2020

(65) Prior Publication Data
US 2022/0193290 A1 Jun. 23, 2022

(30) Foreign Application Priority Data
Apr. 3, 2019 (JP) .................................. 2019-071167

(51) Int. Cl.
*A61L 2/22* (2006.01)
*A61L 2/26* (2006.01)
*G10K 11/34* (2006.01)

(52) U.S. Cl.
CPC ........ *A61L 2/22* (2013.01); *A61L 2/26* (2013.01); *G10K 11/34* (2013.01); *A61L 2202/122* (2013.01); *A61L 2202/23* (2013.01)

(58) Field of Classification Search
CPC ... A61L 2/22; A61L 2/26; A61L 2/186; A61L 2202/122; A61L 2202/23; A61L 2202/15
See application file for complete search history.

(56) References Cited

U.S. PATENT DOCUMENTS 9,180,216 B2 * 11/2015 Kawasaki ............... A61L 2/08

FOREIGN PATENT DOCUMENTS

| JP | H01178041 U | 12/1989 |
| JP | 2004537345 A | 12/2004 |

(Continued)

OTHER PUBLICATIONS

PCT International Search Report, Application No. PCT/JP2020/011721, Jun. 9, 2020, 7 pages.

*Primary Examiner* — Lessanework Seifu
(74) *Attorney, Agent, or Firm* — Quarles & Brady LLP; Yakov S. Sidorin (57) ABSTRACT

A decontamination device configured to provide, on a short time scale, uniform decontamination of target articles without using expensive electron accelerators and to decontaminate such articles in large quantities. The device includes a device body composed of a decontamination region and an aeration region, a conveyance means for conveying an article, a mist supply means, a mist control means, and an aeration means. The mist supply means converts a decontamination agent into a corresponding mist and supplies the mist to the inside of the decontamination region. The mist control means includes vibration boards adjacent to internal wall surfaces of the decontamination region, and these boards are ultrasonically vibrated to generate sound flows from board surfaces by an ultrasound in the vertical direc- (Continued)

tion. The mist inside the decontamination region is pressed by acoustic radiation to concentrate the mist on external surfaces of the article conveyed inside the decontamination region.

7 Claims, 7 Drawing Sheets

(56) References Cited

FOREIGN PATENT DOCUMENTS

| | | | |
|---|---|---|---|
| JP | 2006198120 | A | 8/2006 |
| JP | 2008253937 | A | 10/2008 |
| JP | 2009195563 | A | 9/2009 |
| JP | 2012029859 | A | 2/2012 |
| JP | 2012061403 | A | 3/2012 |

* cited by examiner

CONTINUOUS DECONTAMINATION DEVICE

CROSS-REFERENCE TO RELATED APPLICATIONS

This application represents the US national stage entry from the International Application No. PCT/JP2020/011721, filed on Mar. 17, 2020, that claims priority from the Japanese Patent Application No. JP 2019-071167 filed on Apr. 3, 2019. The disclosure of each of the above-identified patent documents is incorporated by reference herein.

TECHNICAL FIELD

The present invention relates to a continuous decontamination device for continuously decontaminating external surfaces of an article with a decontamination agent mist and conveying the decontaminated article to a working chamber in a sterile environment.

BACKGROUND ART

In consideration of convenience in the clinical environment, pre-filled syringes and pre-filled vials filled with a pharmaceutical product are manufactured. A pharmaceutical product is filled in these syringes or vials in a filling working chamber in a sterile environment (hereinafter referred to as a "sterile working chamber"). Each of the syringes and vials used in this operation is small in size, and such tools to be treated are needed in large numbers. Then, these syringes and vials are sterilized by y-ray irradiation, electron beam irradiation, EOG (ethylene oxide gas), and other approaches at each manufacturing stage, and carried in a sterile working chamber with a predetermined number thereof integrally accommodated in a package.

Illustrative example of the package includes a medical appliance package proposed in the following patent document 1 and disclosed as prior art ("P" in FIG. 1). These packages are generally referred to as "peel-open package", and include a plastic tab (P1 in FIG. 1) molded according to the shape of a medical appliance such as a syringe or vial accommodated therein and a gas-permeable upper surface seal (P2 in FIG. 1). The upper surface seal used is generally Tyvek (trademark) as a non-woven fabric composed of high-density polyethylene microfibers, and the Tyvek (trademark) is gas-permeable through micropores included in the Tyvek (trademark) product to the inside of the plastic tab, but blocks ingress of microorganisms.

The package thus configured is further packed on the exterior with a packaging bag to be circulated and conveyed. However, when the package is circulated or conveyed, or taken out of the packaging bag to carry the same in a sterile working chamber, external surfaces of the plastic tab and the upper surface seal are contaminated. Therefore, the package is not allowed to be carried in the sterile working chamber unless the contaminated external surfaces are decontaminated. Then, after the external surfaces of the plastic tab and the upper surface seal are decontaminated by a decontamination device connected to the sterile working chamber, the package is conveyed to the sterile working chamber, the upper surface seal is peeled open from the plastic tab in the sterile working chamber, and the filling into an internal sterilized syringe or vial is performed.

Generally, various methods using EOG (ethylene oxide gas), hydrogen peroxide (in the form of a gas or mist), ozone gas, plasma, y-ray irradiation, ultraviolet irradiation or electron beam irradiation are introduced for each intended use in a decontamination device for decontaminating an accommodated body carried in the sterile working chamber. One of these methods is the most common method using hydrogen peroxide (in the form of a gas or mist). Advantageously, hydrogen peroxide has a strong sterilization effect, and is inexpensively available and effectively utilized as an environmentally-friendly decontamination agent that is ultimately resolved into oxygen and water. However, a method using hydrogen peroxide is problematic due to longer duration required to obtain a necessary level of decontamination effect. Also, the hydrogen peroxide method unfortunately brings about longer duration required in the aeration operation for removing a condensed film of a hydrogen peroxide solution on the surface of the accommodated body after decontamination.

Meanwhile, in decontamination devices where numerous accommodated bodies are required to be treated per unit time, as shown in production of pre-filled syringes, short-time treatment methods with a high decontamination effect are preferable. The following Non-Patent Document 1 describes a safe decontamination device integrated with a low-energy electron accelerator for obtaining a high decontamination effect as opposed to general devices using a decontamination agent such as hydrogen peroxide, and for providing high productivity and no residue.

In fact, the decontamination device is operated to treat a package that accommodates pre-filled syringes, and the package including a prior-decontaminated syringe is conveyed to a sterile working chamber by a conveyor after external surfaces thereof are decontaminated with electron beams. The device, composed of 3 low-energy electron accelerators (56, 57, 58 in FIG. 2) arranged at an angle of 120 degrees with each other, irradiates with electron beams all the surfaces of the package from irradiation windows (56a, 57a, 58a) in 3 directions.

In this device, a plastic tab and an upper surface seal can efficiently be decontaminated by controlling the dose of the electron beams for irradiation. The following Non-Patent Document 1 describes that this device can treat as many as 3,600 syringes per hour and achieve high productivity.

CITATION LIST

Patent Literature

Patent Document 1: JP-A-4237489

Non-Patent Literature

Non-Patent Document 1: Radiation Application Technology Database, Data Number: 010306 (Prepared by Masayuki Sekiguchi on Oct. 3, 2007), Radiation Application Development Association

SUMMARY OF THE INVENTION

Technical Problem

Figure 2:
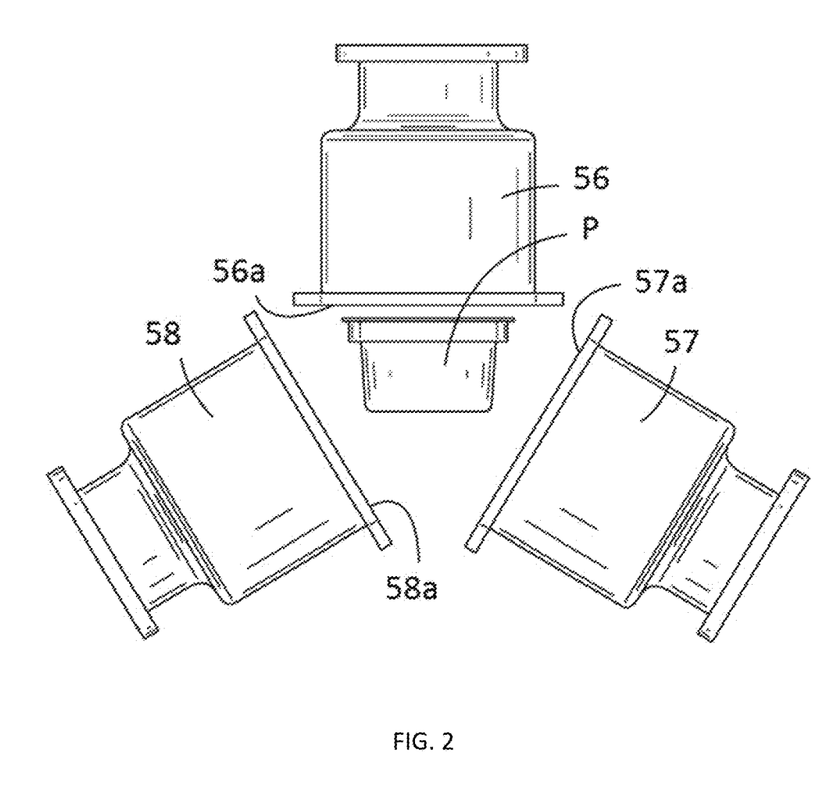
FIG. 2 is a schematic diagram showing the arrangement of electron accelerators of a continuous decontamination device in Non-Patent Document 1.

In the decontamination device in the above Non-Patent Document 1, 3 low-energy electron accelerators, arranged at an angle of 120 degrees with each other on an outer peripheral side of a medical appliance package conveyed in the conveyance direction, irradiate with electron beams at the same time the entire external surfaces of the medical appliance package for decontamination (see FIG. 2).

This method is applicable enough to irradiate with electron beams external surfaces of a medical appliance package (upper surface portion, bottom surface portion and right and left side surface portions). However, this device is insufficient to irradiate with electron beams in that front and rear side surface portions are located apart in the conveyance direction of the medical appliance package. Therefore, it is difficult to maintain a high level of reliability and safety of such a decontamination effect. Thus, the irradiation intensity is required to be higher by making larger irradiation windows of each electron accelerator produced, controlling the irradiation angle and increasing the accelerating voltage of each electron accelerator because the package is distant from the irradiation windows of each electron accelerator when front and rear side surface portions of the medical appliance package are irradiated with electron beams from an outer peripheral portion.

Generally, each low-energy electron accelerator, having a large irradiation area and a potentially higher accelerating voltage, is expensive. In addition, the use limit (service life) of an electron accelerator due to its integrated time in use is shorter when the accelerating voltage is set to be high, resulting in higher maintenance costs by replacement. Therefore, the initial costs and maintenance costs of the device are unfortunately higher due to simultaneous operation of the 3 expensive devices.

Meanwhile, the irradiation intensity varies depending on parts of a medical appliance package, and thus parts close to irradiation windows of an electron accelerator are irradiated with excessive electron beams to cause damage to the medical appliance package when the irradiation intensity of each electron accelerator is set higher to sufficiently decontaminate the front and rear side surface portions of the medical appliance package. In addition, what is problematic is a different decontamination level of each part because the distance between each part of the medical appliance package and irradiation windows of each electron accelerator is different.

Thus, methods using a decontamination agent such as hydrogen peroxide that have recently been used widely are problematic because the decontamination of a medical appliance package requires treatment for a long period of time and in large quantities while they provide effects of strong decontamination, low expenses and environmental friendliness. Meanwhile, the method using an electron accelerator unfortunately causes high device prices and maintenance costs and different decontamination levels at each part, while medical appliance packages requiring treatment in large quantities can effectively be decontaminated.

Thus, the present invention was made in view of the situation to solve the problems, and has an object to provide a continuous decontamination device capable of achieving short-term operations to provide uniform decontamination levels at each part by employing decontamination agents such as hydrogen peroxide that have recently been widely used without using expensive electron accelerators and treating articles to be decontaminated in large quantities.

Solution to the Problem

To solve the aforementioned problem, inventors of the present invention have carried out an extended investigation to find that a decontamination agent mist supplied to a decontamination device is miniaturized or reduced in size by employing ultrasonic vibration and the decontamination agent mist is allowed to concentrate on the surface of an article to be decontaminated in the decontamination device. Based on that technique, the present invention was accomplished.

Specifically, a continuous decontamination device according to an embodiment of the present invention includes, according to description in claim 1, a continuous decontamination device (10) connected to a sterile working chamber (20) for decontaminating external surfaces of an article (P) with a decontamination agent mist (31, 31*a*) and conveying the article to the inside of the sterile working chamber, including a device body (10*a*) composed of a decontamination region (12) and an aeration region (13), a conveyance means (14, 14*a*, 14*b*) for conveying the article, a mist supply means (30), a mist control means (40), and an aeration means, characterized in that the device body includes an inlet (16) for carrying the article before decontamination in the decontamination region and an outlet (18) for carrying the decontaminated article out of the aeration region, the conveyance means conveys the article carried from the inlet to the outlet via the inside of the decontamination region and the aeration region, the mist supply means converts a decontamination agent into a decontamination agent mist, and supplies the same to the inside of the decontamination region, the mist control means includes vibration boards (41, 42, 43, 44, 45, 46) disposed adjacent to internal wall surfaces of the decontamination region, and the vibration boards are ultrasonically vibrated to generate sound flows from board surfaces by an ultrasound in the vertical direction, the decontamination agent mist supplied to the inside of the decontamination region is pressed by acoustic radiation pressure to concentrate the decontamination agent mist on external surfaces of the article conveyed inside the decontamination region by the conveyance means, and the aeration means removes with clean gas the decontamination agent mist that is residual on the external surfaces of the article conveyed by the conveyance means from the decontamination region.

Moreover, an embodiment of the present invention is, according to description in claim 2, the continuous decontamination device according to claim 1, characterized in that the mist control means includes one or more pairs of vibration boards, the pair(s) of vibration boards are arranged with board surfaces thereof being opposite each other from an outer peripheral side of the article conveyed in the conveyance direction by the conveyance means, whereby the decontamination agent mist is controlled to concentrate on the external surfaces of the article by allowing a pressing force by the acoustic radiation pressure to act in the direction of the article conveyed inside the decontamination region.

Furthermore, an embodiment of the present invention includes, according to description in claim 3, the decontamination device according to claim 1 or 2, characterized in that the vibration board includes a base (51) and a plurality of transmitters (53), the plurality of transmitters is arranged on a plain surface (52) of the base so as to be uniform in transmission directions, and the transmitters are operated in the same phase, whereby a sound flow is generated by a significantly directional ultrasound from the board surface of the vibration board in the vertical direction by mutually amplifying the ultrasounds of the plurality of transmitters in the front direction and mutually canceling out the ultrasounds of the plurality of transmitters in the lateral direction.

Moreover, an embodiment of the present invention is, according to description in claim 4, the continuous decontamination device according to any one of claims 1 to 3, characterized in that
the decontamination agent mist supplied to the inside of the decontamination region is further miniaturized by ultrasonic vibration generated from the vibration board.

Moreover, an embodiment of the present invention is, according to description in claim 5, the continuous decontamination device according to any one of claims 1 to 4, characterized in that
the aeration region includes other vibration boards disposed adjacent to internal wall surfaces thereof, and the vibration boards are ultrasonically vibrated to generate sound flows from board surfaces by an ultrasound in the vertical direction, and
a condensed film of the decontamination agent mist that is residual on the external surfaces of the article conveyed inside the aeration region is subjected to ultrasonic vibration by sound flows to promote the aeration efficiency.

Moreover, an embodiment of the present invention is, according to description in claim 6, the continuous decontamination device according to any one of claims 1 to 5, characterized in that
the conveyance means is a conveyor device for placing the article on a bottom wall surface thereof and conveying the same such as a roller conveyor and a mesh conveyor or a support device for supporting a side surface portion of the article and conveying the same such as a timing belt.

Moreover, an embodiment of the present invention is, according to description in claim 7, the continuous decontamination device according to any one of claims 1 to 6, characterized in that
the article to be decontaminated is an accommodated body for accommodating medical appliances such as a sterile syringe or vial.

Advantageous Effects of the Invention

According to the above configuration, the continuous decontamination device of the present invention includes a device body composed of a decontamination region and an aeration region, a conveyance means for conveying an article, a mist supply means, a mist control means, and an aeration means. The device body includes an inlet for carrying the article before decontamination in the decontamination region and an outlet for carrying the decontaminated article out of the aeration region. The conveyance means conveys the article carried from the inlet to the outlet via the inside of the decontamination region and the aeration region.

The mist supply means converts a decontamination agent into a decontamination agent mist, and supplies the same to the inside of the decontamination region. The mist control mechanism includes vibration boards disposed adjacent to internal wall surfaces of the decontamination region, and the vibration boards are ultrasonically vibrated to generate sound flows from board surfaces by an ultrasound in the vertical direction. The decontamination agent mist supplied to the inside of the decontamination region is pressed by acoustic radiation pressure to concentrate the decontamination agent mist on external surfaces of the article conveyed inside the decontamination region by the conveyance means. The aeration means removes with clean gas the decontamination agent mist that is residual on the external surfaces of the article conveyed by the conveyance means from the decontamination region.

Thus, according to the above configuration, the present invention can provide a continuous decontamination device capable of achieving short-term operations to provide uniform decontamination levels at each portion by employing decontamination agents such as hydrogen peroxide that have recently been widely used without using expensive electron accelerators and treating articles to be decontaminated in large quantities.

According to the above configuration, the mist control means may include one or more pairs of vibration boards. The pair(s) of vibration boards are arranged with board surfaces thereof being opposite each other from an outer peripheral side of the article conveyed in the conveyance direction by the conveyance means, whereby the decontamination agent mist is controlled to concentrate on the external surfaces of the article by allowing a pressing force by the acoustic radiation pressure to act in the direction of the article conveyed inside the decontamination region. Thus, the above operational advantage can more specifically be provided.

According to the above configuration, the vibration board includes a base and a plurality of transmitters, and the plurality of transmitters is arranged on a plain surface of the base so as to be uniform in transmission directions, and the transmitters are operated in the same phase. Consequently, the ultrasounds of the plurality of transmitters in the front direction are mutually amplified, and the ultrasounds of the plurality of transmitters in the lateral direction are mutually canceled out. Accordingly, a sound flow can be generated by a significantly directional ultrasound from the board surface of the vibration board in the vertical direction. Thus, the above operational advantage can more specifically be provided.

According to the above configuration, the decontamination agent mist supplied to the inside of the decontamination region is further miniaturized or reduced in size by ultrasonic vibration generated from the vibration board. Accordingly, the above operational advantage can more specifically be provided.

According to the above configuration, the aeration region may include other vibration boards disposed adjacent to internal wall surfaces thereof. These vibration boards are ultrasonically vibrated to generate sound flows from board surfaces by an ultrasound in the vertical direction. Accordingly, a condensed film of the decontamination agent mist that is residual on external surfaces of an article conveyed inside the aeration region is subjected to ultrasonic vibration by sound flows. As a result, evaporation of the condensed film is promoted to improve the aeration efficiency. Thus, the above operational advantage can more specifically be provided.

According to the above configuration, the conveyance means may be a conveyor device for placing the article on a bottom wall surface thereof and conveying the same such as a roller conveyor and a mesh conveyor. The conveyance means may be a support device for supporting a side surface portion of the article and conveying the same such as a timing belt. Accordingly, the above operational advantage can more specifically be provided.

According to the above configuration, the article to be decontaminated may be an accommodated body for accommodating medical appliances such as a sterile syringe or vial. Accordingly, the above operational advantage can more specifically be provided.

DETAILED DESCRIPTION

In the present disclosure, the term "mist" is broadly interpreted as the state of liquid droplet(s) of a decontamination agent miniaturized and floating in the air, the state of a gas and a liquid agent of a decontamination agent in mixture, the state of the decontamination agent to repeat the change in phase between condensation and evaporation of a gas and a droplet, and the like. In terms of particle size as well, the mist is also broadly interpreted to include mists, fogs, and liquid droplets, which can be subclassified.

Accordingly, the mist according to the present invention is categorized into a "mist" (the size may be defined as 10 μm or less) or a "fog" (the size may be defined as 5 μm or less), and a mist having a larger particle size. In the present invention, ultrasonic vibration converts even a mist, a fog and a liquid droplet sized 3 to 10 μm into equalized ultrafine particles 3 μm or less to provide high-level decontamination effects even for a short period of time (later described).

The continuous decontamination device according to the present invention will be described in detail with reference to each embodiment. The present invention is not restricted to each of the following embodiments. In the continuous decontamination device according to each of the following embodiments, a decontamination agent used is a hydrogen peroxide solution. First, an article decontaminated by hydrogen peroxide will be described. In each of the embodiments, an accommodated body (package) for accommodating medical appliances such as a syringe or vial is an article to be decontaminated. In this invention, the article to be decontaminated is not restricted to these accommodated bodies (packages), and it may be used so long as it is continuously decontaminated and conveyed to a sterile working chamber.

First Embodiment

Figure 1:
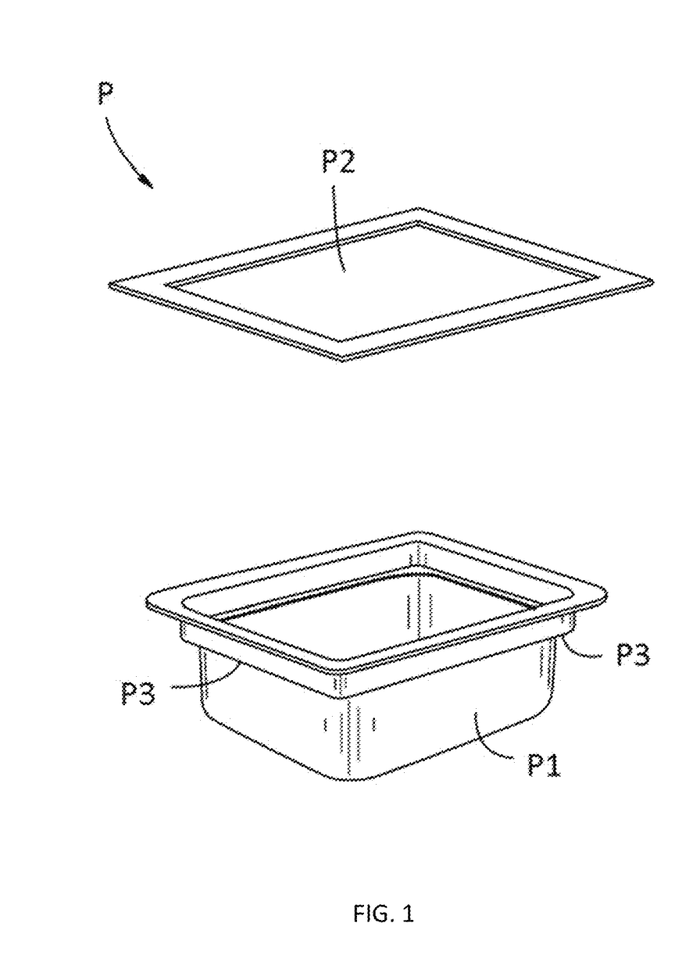
FIG. 1 is a perspective view showing an accommodated body (package) to be decontaminated using a continuous decontamination device according to first and second embodiments.

FIG. 1 is a perspective view showing an accommodated body (package) to be decontaminated used with a continuous decontamination device according to the first embodiment. Nevertheless, in the present invention, the shape of the accommodated body is not restricted to that in FIG. 1 only. In FIG. 1, a package P includes a polyethylene tab P1 and an upper surface seal P2 of Tyvek (trademark). In this first embodiment, numerous sterilized syringes used for filling a pre-filled syringe therein are accommodated and decontaminated in a sealed manner.

Figure 3:
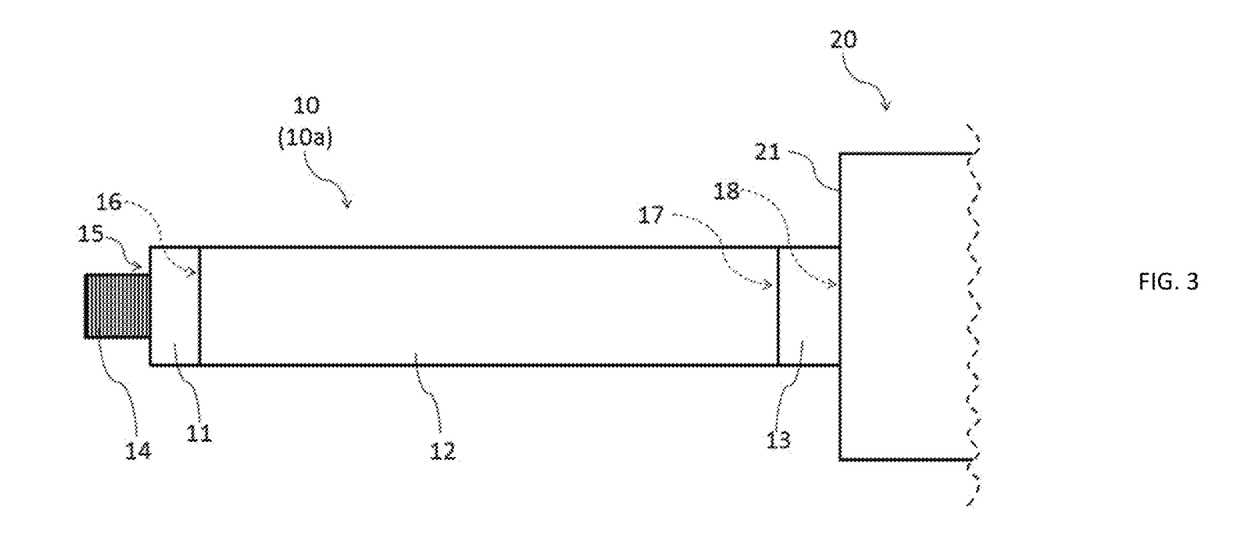
FIG. 3 is a schematic plan view showing the continuous decontamination device according to the first embodiment.
Figure 4:
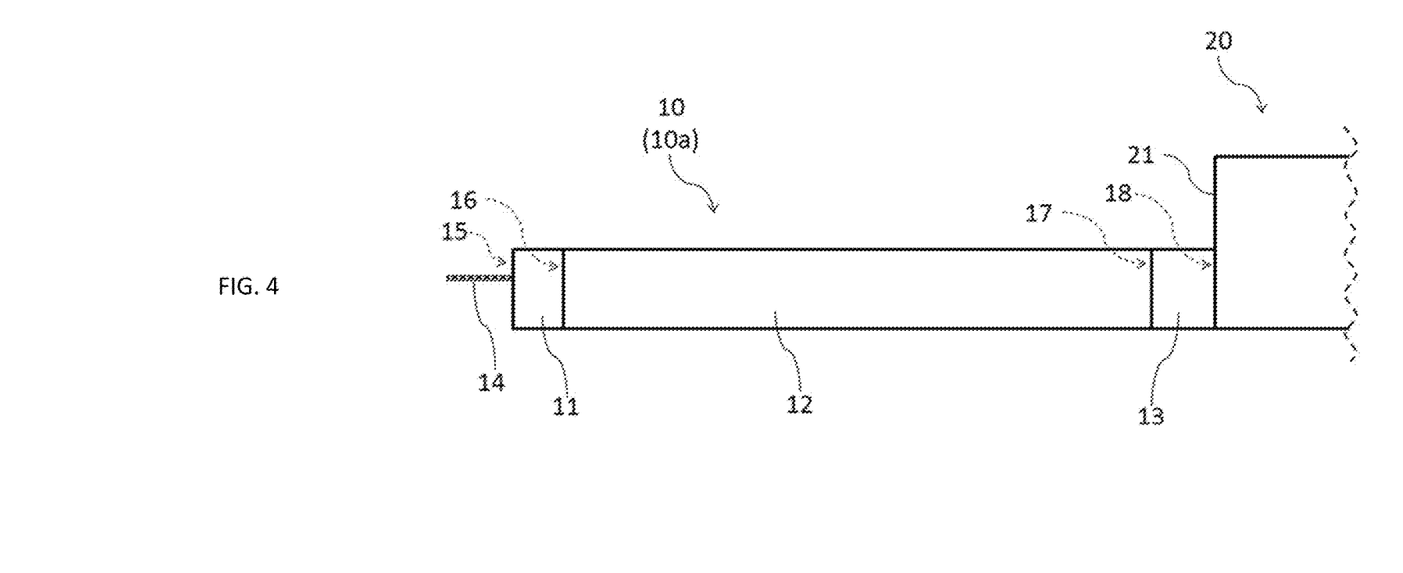
FIG. 4 is a schematic front view showing the continuous decontamination device according to the first embodiment.

Subsequently, the continuous decontamination device according to this first embodiment will be described. FIG. 3 is a schematic plan view showing the continuous decontamination device according to the first embodiment, and FIG. 4 is a schematic plan view showing the continuous decontamination device. The continuous decontamination device according to this first embodiment includes a device body composed of a decontamination region and an aeration region, a roller conveyor for conveying the package P, a mist supply device, a mist control device, and an air supply and exhaust device of clean air for aeration.

As shown in FIGS. 3 and 4, a device body 10a of a continuous decontamination device 10 according to this first embodiment is covered with an outer wall portion made of stainless metal plate on the periphery, linked to a side wall 21 of an isolator 20, and placed on the floor. Also, the device body 10a is divided into an introduction region 11, a decontamination region 12 and an aeration region 13, and is linked such that a wall portion of the aeration region 13 communicates with the side wall 21 of the isolator 20. Inside the device body 10a, a roller conveyor 14 for conveying the package P is disposed inside the isolator 20 from the external environment of the isolator 20 via an inlet 15 of the introduction region 11, the inside of the introduction region 11, an inlet 16 of the decontamination region 12, the inside of the decontamination region 12, an outlet (or the inlet of the aeration region 13) 17 of the decontamination region 12, the inside of the aeration region 13, and an outlet 18 of the aeration region 13 (later described).

Figure 5:
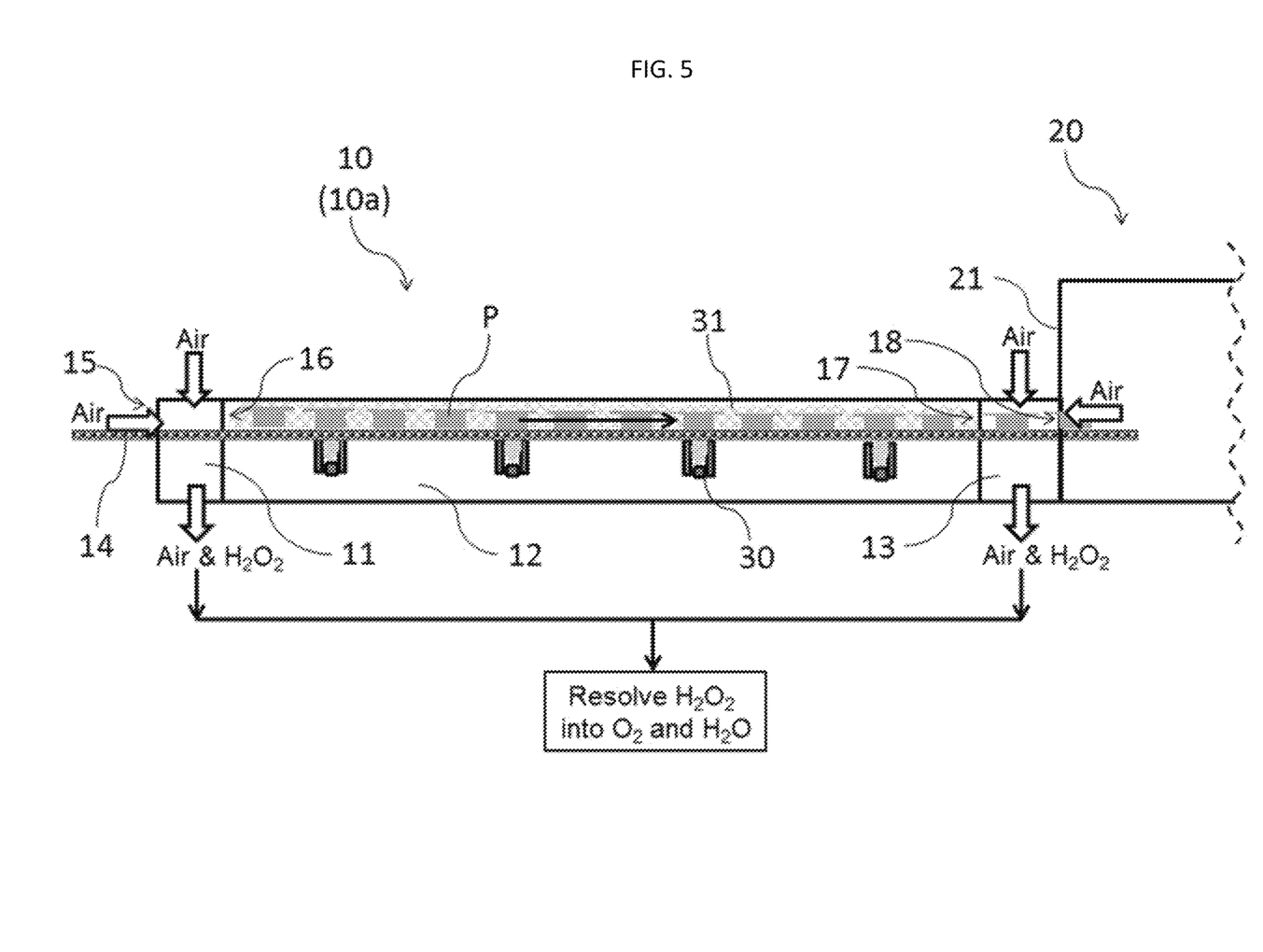
FIG. 5 is a schematic cross-sectional view showing the inside of the schematic front view in FIG. 4.

In such a configuration, the inside of the continuous decontamination device 10 and decontamination operations will be described. FIG. 5 is a schematic cross-sectional view showing the inside of the schematic front view in FIG. 4. In FIG. 5, an operator (not shown) who stays in the external environment places a plurality of packages P on the roller conveyor 14 for driving. The packages P are carried in the inside of the introduction region 11 through the inlet 15 of the introduction region 11, while being placed on the roller conveyor 14 for driving.

Inside the introduction region 11, a hydrogen peroxide solution mist leaks out of the decontamination region 12 through the inlet 16 of the decontamination region 12. Clean air is supplied to the inside of the introduction region 11 and internal air (incl. hydrogen peroxide) is forcibly discharged (an air supply and exhaust device is not shown) such that the leaked hydrogen peroxide solution mist doesn't contaminate the external environment. Preferably, the air in the external environment flows into the inside of the introduction region 11 from the inlet 15 of the introduction region 11 by allowing the forced discharged air to convert the internal pressure of the introduction region 11 into negative pressure that is lower than the external environment. Also, the hydrogen peroxide in the air forcibly discharged from the inside of the introduction region 11 is resolved into oxygen and water by a hydrogen peroxide decomposition unit (not shown).

Subsequently, the packages P are carried in the inside of the decontamination region 12 through the inlet 16 of the decontamination region 12 to be conveyed inside the decontamination region 12 (in the right direction shown). Inside the decontamination region 12, a plurality of mist supply devices 30 (4 devices in FIG. 5) is disposed underneath the roller conveyor 14, and the hydrogen peroxide solution mist 31 is discharged from between the rolls of the roller conveyor 14 toward the packages P conveyed by the roller conveyor 14. As a result, the hydrogen peroxide solution mist 31 is uniformly filled inside the decontamination region 12, particularly at an upper portion of the roller conveyor 14 to continuously decontaminate a plurality of packages P while being conveyed. The mist supply device 30 and the mist control device (not shown in FIG. 5) will be described later. Accordingly, the packages P are uniformly decontaminated entirely on external surfaces thereof by staying for a predetermined period inside the decontamination region 12 while being conveyed by the roller conveyor 14. In addition, the packages P, including a bottom wall portion thereof, are sufficiently decontaminated because they move on a plurality of rolls.

Subsequently, the packages P are carried in the inside of the aeration region 13 through the outlet (or the inlet of the aeration region 13) 17 of the decontamination region 12 to be conveyed inside the aeration region 13 (in the right direction shown). Herein, a hydrogen peroxide thin film is uniformly condensed on external surfaces of the packages P carried in the inside of the aeration region 13 by the roller conveyor 14 (the reason is later described). A hydrogen peroxide solution mist leaks out of the decontamination region 12 to the inside of the aeration region 13 through the inlet 17 of the decontamination region 12. Then, aeration is performed inside the aeration region 13 such that the condensed hydrogen peroxide thin film and the leaked hydrogen peroxide solution mist don't contaminate the inside of the isolator 20.

Specifically, clean air is supplied to the inside of the aeration region 13 by an air supply device (not shown). In addition, the air inside the aeration region 13 (incl. evaporated hydrogen peroxide and hydrogen peroxide solution mist) is forcibly discharged by an air exhaust device (not shown). Also, the hydrogen peroxide in the forcibly discharged air is resolved into oxygen and water by a hydrogen peroxide decomposition unit (not shown). The air supply and exhaust amount of clean air and aeration time in the aeration operation are predetermined conditions. Accordingly, the packages P are conveyed inside the aeration region 13 for aeration and then completely decontaminated.

Subsequently, the packages P are carried in the inside of the isolator 20 through the outlet 18 of the aeration region 13. At this time, the air inside the isolator 20 preferably flows from the outlet 18 of the aeration region 13 into the inside of the aeration region 13 by allowing the forced discharged air in the aeration operation to convert the internal pressure of the aeration region 13 into negative pressure that is lower than the inside of the isolator 20 such that the discharged air in the aeration operation (incl. evaporated hydrogen peroxide and hydrogen peroxide solution mist) doesn't flow into the inside of the isolator 20 through the outlet 18 of the aeration region 13.

Accordingly, in the packages P carried in the inside of the isolator 20 after decontamination, the upper surface seal P2 is peeled open from the package P in the isolator 20 and the packages are filled with syringes or vials sterilized therein.

Figure 6A:
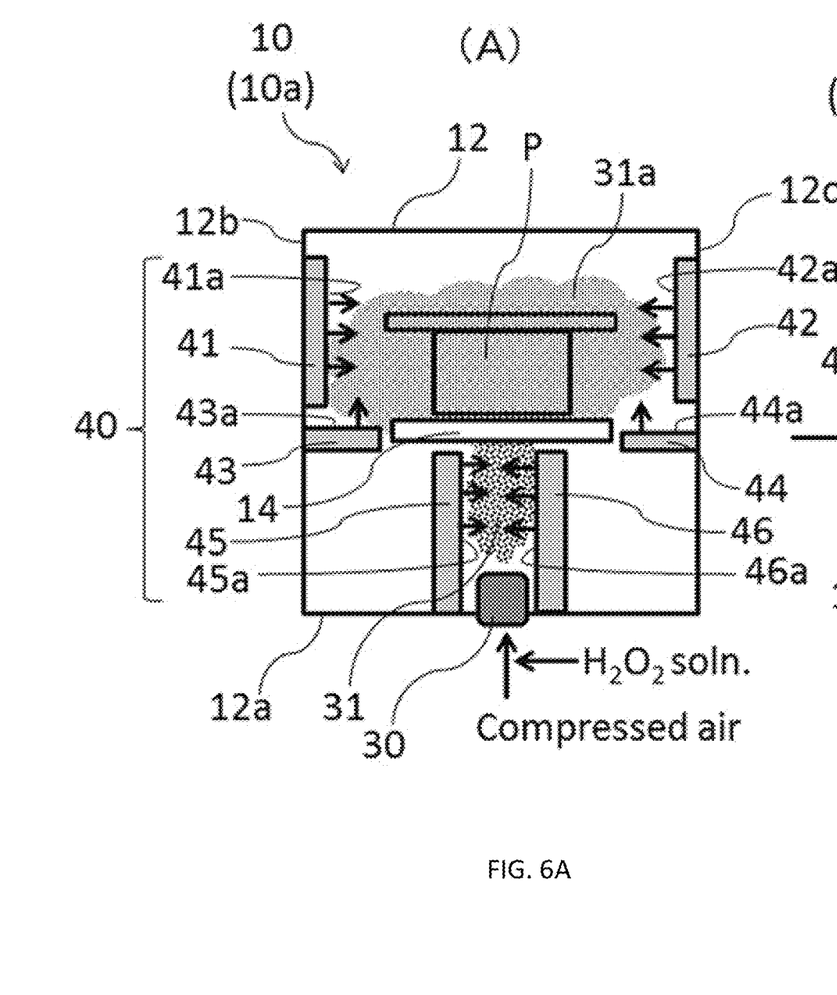
FIG. 6A is a schematic front cross-sectional view and FIG. 6B is a schematic side cross-sectional view, each showing the relationship between a mist supply device and a mist control device according to the first embodiment.
Figure 6B:
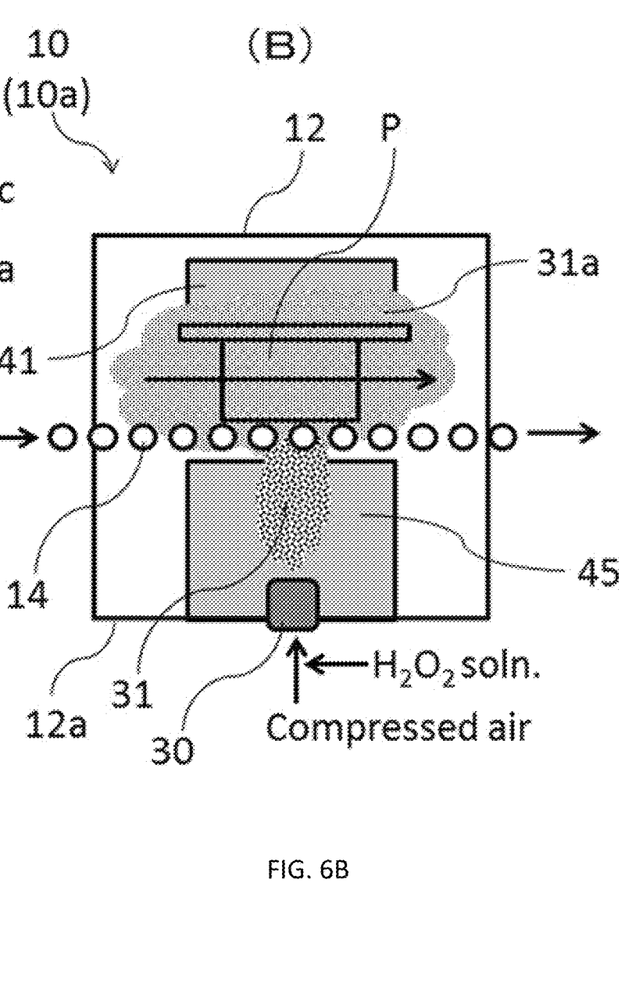

Subsequently, the mist supply device and the mist control device will be described. FIG. 6 is a schematic diagram showing the relationship between the mist supply device and the mist control device according to this first embodiment. FIG. 6A is a front cross-sectional view showing a package P placed on a roller conveyor 14 in the traveling direction. FIG. 6B is a side cross-sectional view showing a package P placed on the roller conveyor 14 in the lateral direction of the traveling direction (in an arrow direction shown).

In FIGS. 6A, 6B, inside the decontamination region 12 of the device body 10a, the package P is placed on the roller conveyor 14 and conveyed. In this first embodiment, a mist supply unit 30 used is a two-fluid spray nozzle 30 disposed on a bottom wall surface 12a of the decontamination region 12. In this first embodiment, the decontamination agent used is a hydrogen peroxide solution ($H_2O_2$ solution). In this first embodiment, 4 two-fluid spray nozzles 30 are used (see FIG. 5).

The two-fluid spray nozzle 30 converts a hydrogen peroxide solution into the hydrogen peroxide solution mist 31 by compressed air from a compressor (not shown) to supply the same to the inside of the decontamination region 12. In the present invention, the mist supply device is not restricted to a two-fluid spray nozzle, and a mist generation means and output are not particularly restricted.

Herein, a mist control device 40 will be described. In this first embodiment, a pair of mist control devices 40 are disposed for one two-fluid spray nozzle 30. In FIG. 6, one two-fluid spray nozzle 30 and a pair of mist control devices 40 will be described. Each of the mist control devices 40 includes 6 vibration boards 41, 42, 43, 44, 45, 46.

Out of the 6 vibration boards, the vibration boards 41, 42 are disposed against the inside of both side walls 12b, 12c of the decontamination region 12 such that vibration surfaces 41a, 42a face in the horizontal direction toward the package P being conveyed by the roller conveyor 14. Also, the vibration boards 43, 44 are disposed with a side surface thereof in contact with the inside of both the side walls 12b, 12c of the decontamination region 12 such that vibration surfaces 43a, 44a face toward an upper portion of the decontamination region 12 (above the roller conveyor 14). In addition, the vibration boards 45, 46 are disposed with a bottom side surface thereof in contact with the inside of the bottom wall surface 12a of the decontamination region 12 such that vibration surfaces 45a, 46a face in the horizontal direction toward the hydrogen peroxide solution mist 31 supplied from the two-fluid spray nozzle 30.

Figure 7:
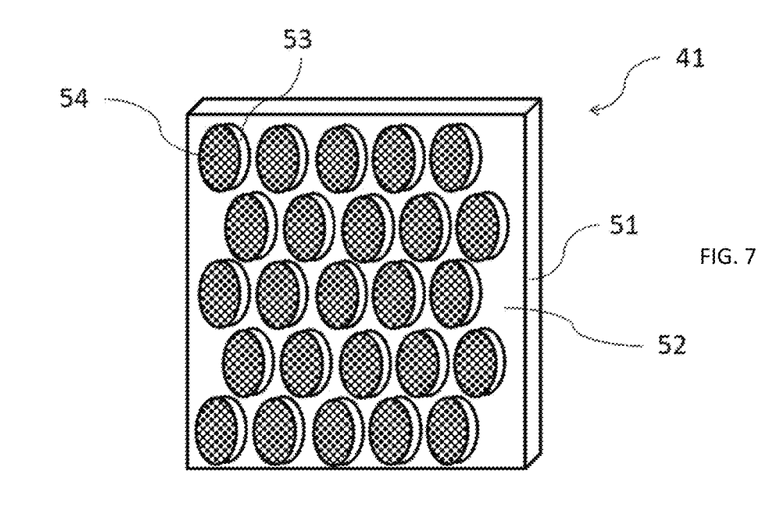
FIG. 7 is a schematic perspective view showing a plurality of ultrasonic speakers arranged in a speaker base in vibration boards according to the first embodiment.

Herein, the vibration board 41 will be described (also applied to the vibration boards 42, 43, 44, 45, 46). FIG. 7 is a schematic perspective view showing a plurality of ultrasonic speakers arranged in a speaker base in a vibration board included in the mist control device 40 in FIG. 6. In FIG. 7, the vibration board 41 includes a base and a plurality of transmitters. In this first embodiment, the base used is a speaker base 51, and the transmitter used is an ultrasonic speaker 53. In this first embodiment, 25 ultrasonic speakers 53 are arranged on a plain surface 52 of the speaker base 51 so as to be uniform in transmission direction of a vibration surface 54 (leftward as seen from the front shown). The number of ultrasonic speakers is not particularly restricted.

In this first embodiment, the ultrasonic speaker 53 used is an ultra directional ultrasonic speaker. Specifically, ultrasonic speakers (DC12V, 50 mA) of frequency modulation system transmitting a frequency near 40 KHz are used. The type, size, structure and output of the ultrasonic speaker are not particularly restricted. In the present invention, the vibration board included in the mist control device is not restricted to an ultrasonic speaker, and the ultrasonic generation means, frequency range and output are not particularly restricted.

In this first embodiment, a plurality of (25) ultrasonic speakers 53 are arranged so as to be uniform in transmission direction of the vibration surface 54, and the transmitters are operated in the same phase to mutually amplify ultrasounds from the plurality of ultrasonic speakers 53 in the front direction and mutually cancel out ultrasounds from the plurality of ultrasonic speakers 53 in the lateral direction. Consequently, the ultrasonic speakers 53 arranged on the speaker base 51 are ultrasonically vibrated to generate a significantly directional sound flow traveling in the air from each of the vibration surfaces 54 in the vertical direction. The frequency and output of the ultrasonic speakers 53 are controlled by an ultrasonic controller (not shown) to achieve efficient decontamination operations.

Herein, alternatives of the conveyance means according to this first embodiment will be described. In the above description, the conveyance means used is the roller conveyor 14 for placing a packages P on a bottom wall surface thereof and conveying the same. However, the conveyance means is not restricted thereto, and other conveyor devices for placing a packages P on a bottom wall surface thereof and conveying the same in a similar fashion, such as a mesh conveyor, may be used. Support devices for supporting a side surface portion of the package P and conveying the same, such as a timing belt, may also be used.

Figure 8:
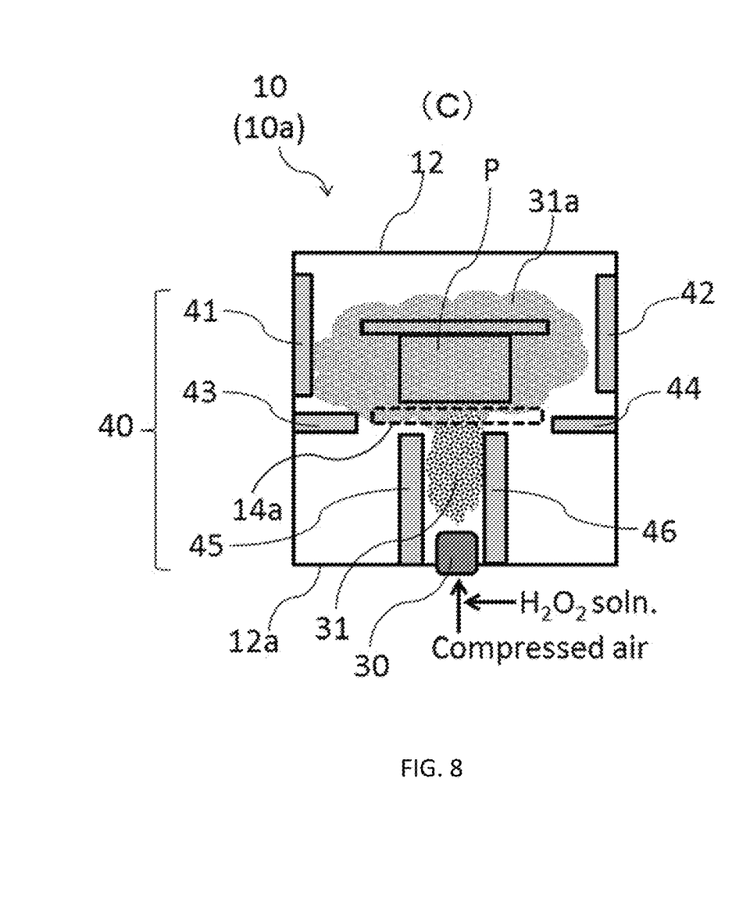
FIG. 8 is a front cross-sectional view showing an alternative of a conveyance means in the schematic diagram showing the relationship between the mist supply device and the mist control device in FIG. 6.

FIG. 8 is a front cross-sectional view showing an alternative of a conveyance means in a schematic diagram showing the relationship between the mist supply device and the mist control device in FIG. 6. In FIG. 8 (C), the conveyance means used is a mesh conveyor 14a. In this case, the two-fluid spray nozzle 30 discharges the hydrogen peroxide solution mist 31 from between the meshes of the mesh conveyor 14a toward the package P conveyed by the mesh conveyor 14a. As a result, the hydrogen peroxide solution mist 31 is uniformly filled inside the decontamination region 12, particularly above the roller conveyor 14 to continuously decontaminate a plurality of packages P while being conveyed. The bottom wall portion of the package P moves while being placed on the meshes, and the bottom wall portion of the package P that is in contact with the mesh conveyor 14a is believed to sufficiently be decontaminated through resonance with ultrasonic vibration by later-described vibration boards.

Figure 9:
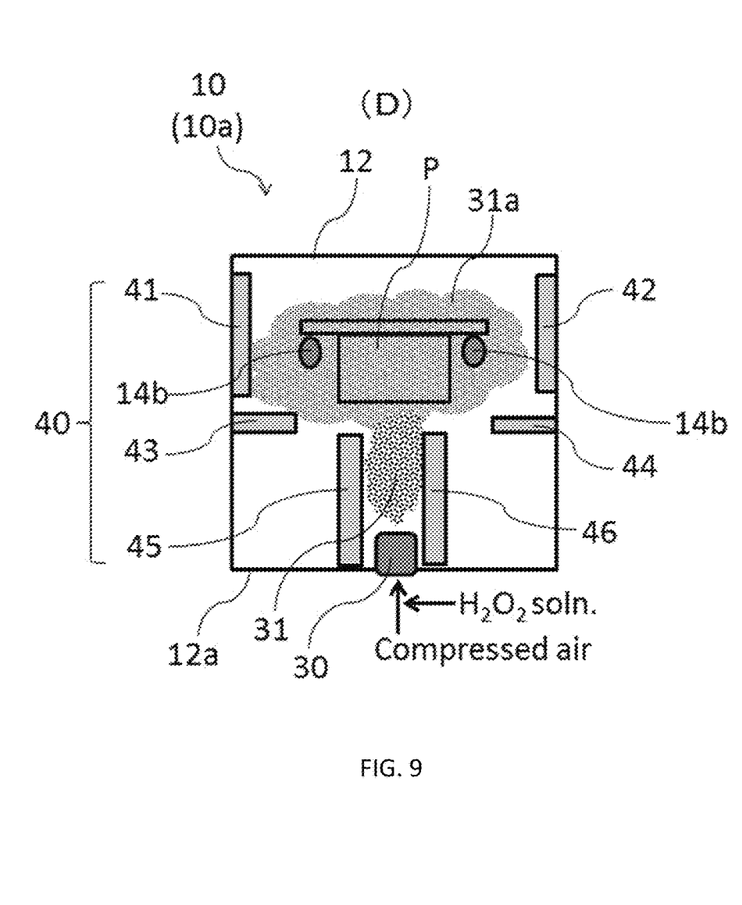
FIG. 9 is a front cross-sectional view showing other alternative of the conveyance means in the schematic diagram showing the relationship between the mist supply device and the mist control device in FIGS. 6A, 6B.

FIG. 9 is a front cross-sectional view showing other alternative of a conveyance means in a schematic diagram showing the relationship between the mist supply device and the mist control device in FIG. 6. In FIG. 9 (D), the conveyance means used is a timing belt 14b. 2 timing belts 14b support both shoulder portions of the package P traveling in the traveling direction from both side surface portions and convey the same. In this case, the two-fluid spray nozzle 30 directly discharges the hydrogen peroxide solution mist 31 toward the package P conveyed by the timing belt 14b. As a result, the hydrogen peroxide solution mist 31 is uniformly filled inside the decontamination region 12, particularly above the roller conveyor 14 to continuously decontaminate a plurality of packages P while being conveyed. The both shoulder portions of the package P are supported by the timing belt 14b with less contact surface, and it is believed that they are sufficiently decontaminated through resonance with ultrasonic vibration by later-described vibration boards.

Subsequently, the action of the hydrogen peroxide solution mist 31 inside the decontamination region 12 including the mist supply device 30 and the mist control device 40 according to the above configuration will be described with reference to FIG. 6. In FIG. 6, one two-fluid spray nozzle 30 and 6 vibration boards 41, 42, 43, 44, 45, 46 are disposed inside the decontamination region 12. Also, the package P is placed on the roller conveyor 14 and conveyed.

Ultrasonic vibration of the ultrasonic speaker 53 of each of the vibration boards in this state generates significantly directional sound flows traveling in the vertical direction from the 6 vibration surfaces 41a, 42a, 43a, 44a, 45a, 46a respectively (indicated by arrows from board surfaces). The sound flows generated from the vibration surfaces 45a, 46a of the vibration boards 45, act on the hydrogen peroxide solution mist 31 discharged from the two-fluid spray nozzle 30. The hydrogen peroxide solution mist 31 travels upward (an upper portion of the decontamination region 12) by a releasing pressure from the two-fluid spray nozzle 30. At this time, the hydrogen peroxide solution mist 31 is converted into a fine mist 31a miniaturized by the ultrasonic vibration by the sound flows generated from the vibration surfaces 45a, 46a, and travels toward the periphery of the package P from between the rolls of the roller conveyor 14.

Subsequently, at an upper portion of the roller conveyor 14, sound flows generated from the vibration surfaces 41a, 42a of the vibration boards 41, 42 act on the fine mist 31a miniaturized by ultrasonic vibration by the vibration surfaces 45a, 46a to highly miniaturized the mist. Also, sound flows generated from the vibration surfaces 43a, 44a of the vibration boards 43, 44 similarly act on the fine mist 31a to highly miniaturized the mist.

Inventors of the present invention found that in this state the fine mist 31a highly miniaturized by ultrasonic vibration from the vibration surfaces 41a, 42a, 43a, 44a concentrates on the periphery of the package P placed on the roller conveyor 14 (see FIGS. 6A, 6B). The reason has not clearly been identified, but this is probably because acoustic waves generated from each vibration board reach the package P but only part of the waves reflects off the same to absorb or scatter primarily on the surface of the package P, thereby allowing the pressing force by the acoustic radiation pressure to concentrate in the package P's direction.

In fact, since the fine mist 31a is miniaturized by ultrasonic vibration to have smaller particle sizes and larger surface areas, it is believed that the evaporation efficiency of mists is high, resulting in repeated evaporation and condensation. The fine mist 31a is a highly-miniaturized mist to concentrate on external surfaces of the package P and form a uniform and thin condensed film on the external surfaces of the package P. Therefore, no excessive condensation occurs on internal wall surfaces of the decontamination region 12 and each roll of the roller conveyor 14.

Thus, the fine mist 31a of hydrogen peroxide is subjected to constant ultrasonic vibration to concentrate on the periphery of the package P conveyed with repeated evaporation, condensation, and miniaturization. Even on the external surfaces of the package P, the fine mist 31a is subjected to constant ultrasonic vibration to cause repeated re-evaporation and condensation of a uniform and thin condensed film. Accordingly, it is believed that ultrafine particles of hydrogen peroxide 3 nm or less and a hydrogen peroxide gas are subjected to phase change for coexistence on the periphery of the package P to provide high-level decontamination environment.

Also, by repeated re-evaporation and condensation of the uniformly and thinly formed condensed film on the external surfaces of the package P, the concentration of a decontamination agent in a decontamination mist can be increased and efficient decontamination can be performed with a small amount of decontamination agent. Such an efficient decontamination with a small amount of decontamination agent can improve the efficiency of aeration for a condensed film of the fine mist 31a that is residual on the surface of the package P and reduce the duration of decontamination operations.

Subsequently, the reliability of decontamination effect and the possibility to shorten the decontamination time inside the decontamination region 12 including the mist supply device 30 and the mist control device 40 according to the above configuration are confirmed by examples.

Example

In this example, a "decontamination unit" including one two-fluid spray nozzle 30 and 6 vibration boards 41, 42, 43, 44, 45, 46 shown in FIG. 6 is used, and a package P is placed on rolls of a roller conveyor 14 without movement, and the decontamination time was confirmed under predetermined conditions. In the following example, the package P used has the dimensions of 250 mm in length, 240 mm in width and 120 mm in height.

Figure 10A:
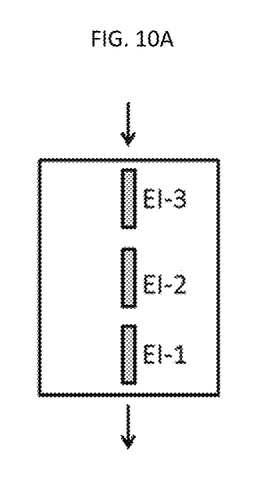
FIGS. 10A, 10B, 10C present diagrams showing a position of an enzyme indicator (EI) applied on external surfaces of a package P in an example.
Figure 10B:
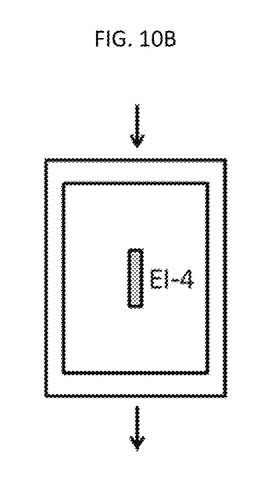
Figure 10C:
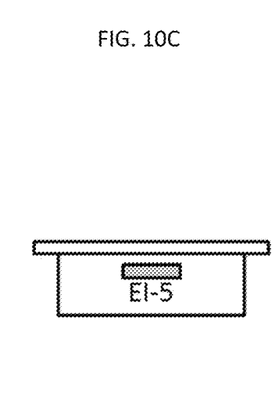

Decontamination effects on external surfaces of the package P were confirmed by an enzyme indicator (EI). EI is an apparatus for fluorescence assay of residual enzymatic activity after a test to confirm decontamination effects, and this approach is advantageous in removing culture operations in conventional biological indicator (BI) and reducing the duration of operations. EI's comparative equality with BI was recently confirmed and the EI technique has proactively been used. The log spore reduction (LRD) value was calculated by the logarithmic decrement of fungi from the EI's fluorescence intensity after decontamination, and the LRD of 4 to 6 or more was judged as a sufficiently acceptable decontamination standard effect. EI-1 to EI-3 were disposed at 3 locations on upper external surfaces of the package P, EI-4 at one location on a bottom surface, and EI-5 at one location on one side surface (see FIGS. 10A, 10B, 10C).

In this example, the input of a hydrogen peroxide solution (35 W/V %) into the decontamination unit was determined by 2 standards: an operating time for decontamination of 3 minutes (decontamination time 2.5 minutes+aeration time 0.5 minutes) and an operating time for decontamination of 5 minutes (decontamination time: 4 minutes+aeration time: one minute), decontaminated at a uniform input speed of 5.6 g/min. The input of hydrogen peroxide solution for each of the standards corresponded to 300 g/m$^2$ and 500 g/m$^2$. One standard was defined as a Comparative Example: an operating time for decontamination of 5 minutes without operating a mist control device 40 (vibration board). Table 1 shows the LRD values of EI-1 to EI-5 of Example and Comparative Example after decontamination operation.

TABLE 1

| | Decontamination operation (min) | Decontamination time (min) | Aeration (min) | Vibration board | LRD value | | | | |
|---|---|---|---|---|---|---|---|---|---|
| | | | | | Upper surface | | | Bottom surface | Side surface |
| | | | | | EI-1 | EI-1 | EI-1 | EI-1 | EI-1 |
| Condition 1 | 3 | 2.5 | 0.5 | ON | — | <2.5 | — | 3.0 | 3.8 |
| Condition 2 | 5 | 4 | 1 | ON | 6.5 | 5.1 | 8.7 | 8.7 | 6.9 |
| Condition 3 | 5 | 4 | 1 | OFF | — | <2.5 | — | 7.4 | <2.5 |

As shown in Table 1, in cases where the input of a hydrogen peroxide solution is 5.6 g/min, the LRD values entirely on external surfaces of a package P were to 6 or more, indicating sufficient decontamination effects under a condition of an operating time for decontamination of 5 minutes (decontamination time: 4 minutes+aeration time: one minute) (condition 2). It is found that under the condition (condition 2), the entire external surfaces of the package P are uniformly decontaminated. On the other hand, in the Comparative Example where decontamination was performed without operating vibration boards (condition 3), insufficiently decontaminated regions having an LRD of less than 4 were confirmed on the upper surface and the side surface using the same operating time for decontamination of 5 minutes (decontamination time: 4 minutes+aeration time: one minute). Also, under the condition of an operating time for decontamination of 3 minutes (decontamination time 2.5 minutes+aeration time 0.5 minutes) (condition 1) by operating the vibration boards, a decontamination effect was insufficient.

From these results, for example, when a continuous decontamination device having one line of a decontamination region 4000 mm and an aeration region 1000 mm is designed by employing the condition 2, about 15 packages (250 mm in length, 240 mm in width and 120 mm in height), each accommodating 100 vials or syringes, can be accommodated in the device, and can be decontaminated with 5-minute retention per package. In other words, in this line, 3 packages can be decontaminated for one minute, meaning that 300 vials or syringes can be conveyed to an isolator per minute. In addition, the length and the number of the conveyance lines can be increased to achieve shorter and more compact packages, thereby allowing more and more vials or syringes to be conveyed to an isolator.

Second Embodiment

Figure 11A:
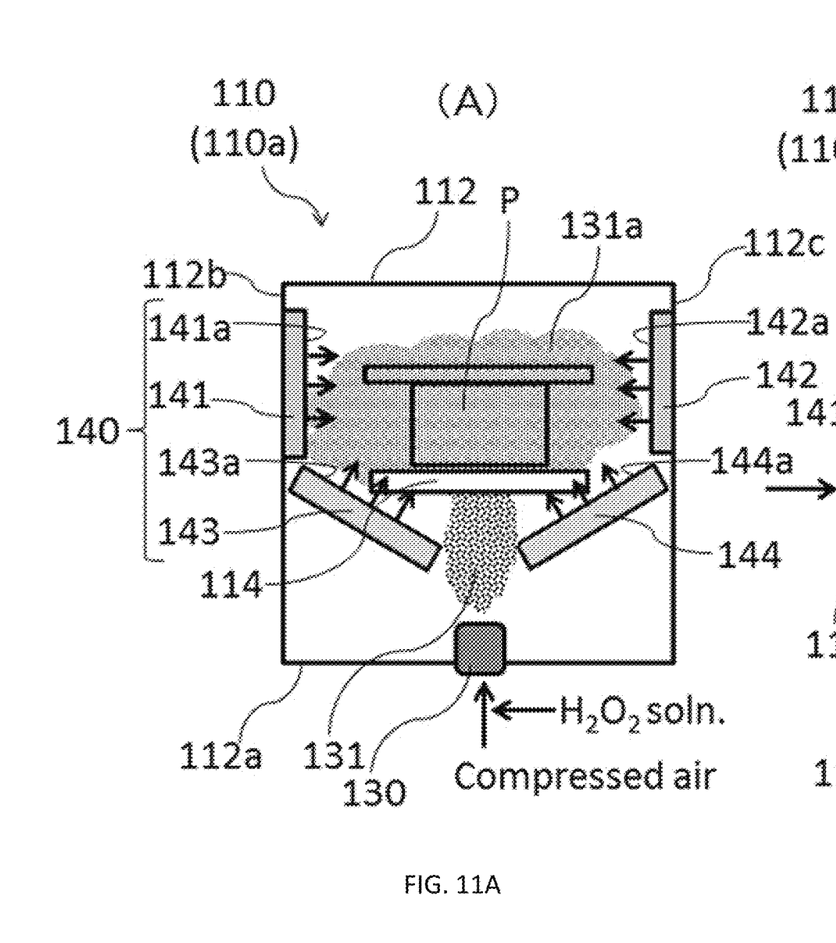
FIG. 11A is a schematic front cross-sectional view and FIG. 11B is a schematic side cross-sectional view showing the relationship between a mist supply device and ae mist control device according to a second embodiment.
Figure 11B:
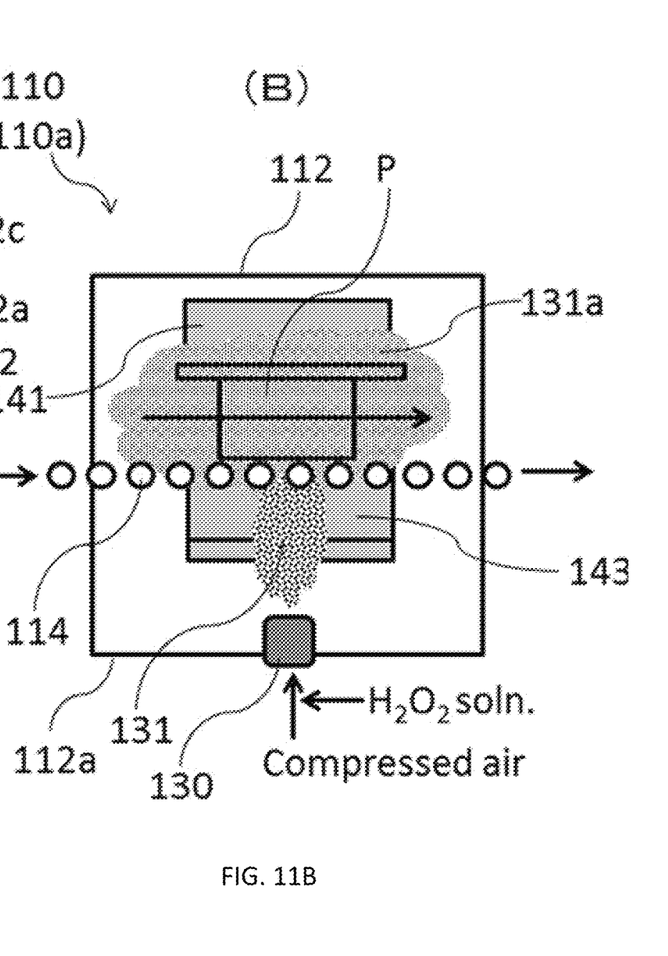

In this second embodiment, the number and arrangement of vibration boards of the mist control device for the above first embodiment were altered. FIG. 11 is a cross-sectional view showing the relationship between a mist supply device and a mist control device according to this second embodiment. FIG. 11(A) is a front cross-sectional view showing a package P placed on a roller conveyor 114 in the traveling direction. FIG. 11(B) is a side cross-sectional view showing packages P placed on the roller conveyor 114 in the lateral direction of the traveling direction (in direction shown by an arrow).

In FIGS. 11A, 11B, inside a decontamination region 112 of a device body 110*a*, the package P is placed on the roller conveyor 114 and conveyed. In this second embodiment, a mist supply device 130 used is a two-fluid spray nozzle 130, as in the above first embodiment, which is disposed on a bottom wall surface 112*a* of the decontamination region 112. Even in this second embodiment, the decontamination agent used is a hydrogen peroxide solution ($H_2O_2$ solution) as well as in the above first embodiment.

The two-fluid spray nozzle 130 converts a hydrogen peroxide solution into a hydrogen peroxide solution mist 131 by compressed air from a compressor (not shown) to supply the same to the inside of the decontamination region 112. In the present invention, the mist supply device is not restricted to a two-fluid spray nozzle, and a mist generation means and output are not particularly restricted.

Herein, a mist control unit 140 will be described. In this second embodiment, a pair of mist control devices 40 are disposed for one two-fluid spray nozzle 130. In FIG. 11, one two-fluid spray nozzle 130 and a pair of mist control devices 140 will be described. Each mist control device 140 includes 4 vibration boards 141, 142, 143, 144.

The vibration boards 141, 142 out of the 4 vibration boards are disposed against the inside of both side walls 112*b*, 112*c* of the decontamination region 112 such that vibration surfaces 141*a*, 142*a* face in the horizontal direction toward packages P being conveyed on the roller conveyor 114 as well as in the above first embodiment. Also, the vibration boards 143, 144 are disposed with a side surface thereof in contact with the inside of the both side walls 112*b*, 112*c* of the decontamination region 112 such that vibration surfaces 143*a*, 144*a* face diagonally upward toward an upper portion of the decontamination region 112 (above the roller conveyor 114).

The structure of the vibration boards 141, 142, 143, 144 is the same as that of a plurality of (25) ultrasonic speakers arranged in the speaker base described in the above first embodiment (see FIG. 7).

Vibration boards were arranged in an aeration region in order to further improve the aeration efficiency in this second embodiment (not shown), which are, however, not employed in this first embodiment. As to vibration boards in this second embodiment, 2 vibration boards were arranged at the same position as the vibration boards 141, 142 in the decontamination region 112 (see FIG. 11). Accordingly, in the aeration region, clean air is supplied and discharged, and ultrasonic vibration by sound flows acts on external surfaces of a package P to promote evaporation of a condensed film of a fine mist 131*a* composed of hydrogen peroxide. As a result, the aeration efficiency can be improved.

Subsequently, the action of the hydrogen peroxide solution mist 131 inside the decontamination region 112 including the mist supply device 130 and the mist control device 140 according to the above configuration will be described with reference to FIG. 11. In FIG. 11, one two-fluid spray nozzle 130 and 4 vibration boards 141, 142, 143, 144 are disposed inside the decontamination region 112. Also, the package P is placed on the roller conveyor 114 and conveyed.

Ultrasonic vibration of the ultrasonic speaker 53 of each of the vibration boards in this state (see FIG. 7) generates significantly directional sound flows traveling in the vertical direction from the 4 vibration surfaces 141*a*, 142*a*, 143*a*, 144*a* respectively (indicated by arrows from board surfaces). The hydrogen peroxide solution mist 131 discharged from the two-fluid spray nozzle 130 travels upward (an upper portion of the decontamination region 112) by a releasing pressure from the two-fluid spray nozzle 130, and travels toward the periphery of the package P from between the rolls of the roller conveyor 114.

Subsequently, at an upper portion of the roller conveyor 114, sound flows generated from the vibration surface 141*a*, 142*a* of the vibration boards 141, 142 act on the hydrogen peroxide solution mist 131 to miniaturized the fine mist 131*a*. Also, sound flows generated from the vibration surfaces 143*a*, 144*a* of the vibration boards 143, 144 similarly act on the fine mist 131*a* to highly miniaturized the mist.

Inventors of the present invention found that in this state the fine mist 131*a* highly miniaturized by ultrasonic vibration from the vibration surfaces 141*a*, 142*a*, 143*a*, 144*a* concentrates on the periphery of the package P placed on the roller conveyor 114 (see FIG. 11). The reason has not clearly been identified, but this is probably because acoustic waves generated from each vibration board reach the package P but only part of the waves reflects off the same to absorb or scatter primarily on the surface of the package P, thereby allowing the pressing force by the acoustic radiation pressure to concentrate in the package P's direction.

In fact, since the fine mist 131*a* is miniaturized by ultrasonic vibration to have smaller particle sizes and larger surface areas, it is believed that the evaporation efficiency of mists is high, resulting in repeated evaporation and condensation. The fine mist 131*a* is a highly-miniaturized mist to concentrate on the external surfaces of the package P and form a uniform and thin condensed film on the external surfaces of the package P. Therefore, no excessive condensation occurs on internal wall surfaces of the decontamination region 112 and each roll of the roller conveyor 114.

Thus, the fine mist 131*a* of hydrogen peroxide is subjected to constant ultrasonic vibration to concentrate on the periphery of the package P conveyed with repeated evaporation, condensation, and miniaturization. Even on the external surfaces of the package P, the fine mist 131*a* is subjected to constant ultrasonic vibration to cause repeated re-evaporation and condensation of a uniform and thin condensed film. Accordingly, it is believed that ultrafine particles of hydrogen peroxide 3 μm or less and a hydrogen peroxide gas are subjected to phase change for coexistence on the periphery of the package P to provide high-level decontamination environment.

Also, by repeated re-evaporation and condensation of the uniformly and thinly formed condensed film on the external surfaces of the package P, the concentration of a decontamination agent in a decontamination mist can be increased and efficient decontamination can be performed with a small amount of decontamination agent. Such an efficient decontamination with a small amount of decontamination agent can improve the efficiency of aeration after decontamination and reduce the duration of decontamination operations.

Thus, according to each of the above embodiments, the present invention can provide a continuous decontamination device capable of achieving short-term operations to provide uniform decontamination levels at each portion by employing decontamination agents such as hydrogen peroxide that have recently been widely used without using expensive electron accelerators and treating articles to be decontaminated in large quantities.

The goals of the present invention are achieved by not only each of the above embodiments, but also by the following various alternatives.

(1) In the above first embodiment, 6 vibration boards are combined for one two-fluid spray nozzle. In the above second embodiment, 4 vibration boards are combined for one two-fluid spray nozzle. However, the combination is not restricted to these, and 2 to 6, or more vibration boards disposed on right and left sides of a package or at other parts may be combined for continuous decontamination.

(2) In each of the above embodiments, no vibration boards are arranged at an upper portion of the package. However, the configuration is not restricted thereto, and vibration boards may be arranged on an upper wall surface of the decontamination region to provide ultrasonic vibration for an upper surface of the package by acoustic waves.

(3) In the above first embodiment, 2 vibration boards (45, 46) are arranged at a position where a two-fluid spray nozzle discharges a hydrogen peroxide solution mist to allow ultrasonic vibration to act thereon. Thereafter, a miniaturized mist is discharged toward the package. However, the configuration is not restricted thereto, and a mist may be guided with a guide plate for a mist in the direction of the package without arranging vibration boards at a position where a hydrogen peroxide solution mist is discharged.

(4) In the above first embodiment, vibration surfaces of 2 vibration boards (43, 44) are arranged in the vertical direction toward an upper portion of the decontamination region 12 to allow ultrasonic vibration to act thereon. However, the configuration is not restricted thereto, and a hydrogen peroxide solution mist may be controlled without arranging vibration boards in the vertical direction.

(5) In the above first embodiment, no vibration boards are arranged in an aeration region. In the above second embodiment, vibration boards are arranged in the aeration region. However, the combination is not restricted thereto, and the arrangement of vibration boards in the aeration region may optionally be determined by selecting the device length of an aeration region or the like as required.

(6) In the above embodiment, 4 two-fluid spray nozzles and vibration boards corresponding thereto are arranged in a decontamination region. However, the arrangement is not restricted thereto, and 5 or more or 3 or less two-fluid spray nozzles and vibration boards corresponding thereto may be arranged according to the speed of decontamination operations.

(7) In each of the above embodiments, a mist supply device used is a two-fluid spray nozzle. However, the mist supply device is not restricted thereto, and an ultrasonic humidifier (nebulizer) or a single-fluid spray nozzle may be used. Also, a combination of a plurality of mist supply devices may be used.

(8) In each of the above embodiments, a vibration board of a mist control device used includes a plurality of ultrasonic speakers arranged in a speaker base. However, the vibration board is not restricted thereto, and any type of vibration board may be used so long as it includes a Langevin type transducer fixed to a stainless steel having a constant area or a board surface for ultrasonic vibration.

(9) In each of the above embodiments, vibration boards of a mist circulation dispersion unit used include a plurality of ultrasonic speakers arranged in a speaker base so as to be uniform in transmission directions of the ultrasonic speakers, and the ultrasonic speakers are operated in the same phase. However, the vibration boards are not restricted thereto, and a plurality of ultrasonic speakers may be operated in a different phase.

(10) In the above embodiments, the decontamination agent used is a hydrogen peroxide solution ($H_2O_2$ solution). However, the decontamination agent is not restricted thereto, and it may be any type of decontamination agent so long as it is liquid.

REFERENCE SIGNS LIST

10, 110 . . . Continuous decontamination device, 10*a*, 110*a* . . . Device body,
11 . . . Introduction region, 12, 112 . . . Decontamination region,
13 . . . Aeration region,
14, 114 . . . Roller conveyor,
14*a* . . . Mesh conveyor, 14*b* . . . Timing belt,
15, 16 . . . Inlet, 17, 18 . . . Outlet,
20 . . . Isolator, 21 . . . Side wall,
30, 130 . . . Mist supply device (Two-fluid spray nozzle),
40, 140 . . . Mist control device,
31, 131 . . . Hydrogen peroxide solution mist, 31*a*, 131*a* . . . Fine mist,
41, 42, 43, 44, 45, 46, 141, 142, 143, 144 . . . Vibration board,
41*a*, 42*a*, 43*a*, 44*a*, 45*a*, 46*a* . . . vibration surface,
51 . . . Speaker base, 52 . . . Plain surface of speaker base,
53 . . . Ultrasonic speaker, 54 . . . Vibration surface of ultrasonic speaker,
P . . . Package, P1 . . . Tab, P2 . . . Upper surface seal, P3 . . . Side surface shoulder portion,
EI-1 to EI-5 . . . Enzyme indicator.

The invention claimed is:

1. A continuous decontamination device configured to decontaminate external surfaces of an article with a decontamination agent mist and to convey the article into a sterile working chamber to which the device is connected in operation, the device comprising:

a device body composed of a decontamination region and an aeration region, a conveyance means for conveying the article, a mist supply means, a mist control means, and an aeration means, wherein:

the device body includes an inlet dimensioned to deliver the article into the decontamination region before decontamination, and an outlet dimensioned to remove the article that has been decontaminated out of the aeration region, the conveyance means is configured to convey the article carried from the inlet to the outlet via an inside of the decontamination region and the aeration region, the mist supply means is configured to convert a decontamination agent into the decontamination agent mist, and to supply the decontamination agent mist to the inside of the decontamination region, the mist control means includes vibration boards disposed adjacent to internal wall surfaces of the decontamination region, the vibration boards being configured to be ultrasonically vibrated to generate sound flows from board surfaces by an ultrasound in the vertical direction to press the decontamination agent mist by acoustic radiation pressure to concentrate the decontamination agent mist on external surfaces of the article conveyed inside the decontamination region by the conveyance means, and the aeration means is configured to remove a residue of the decontamination agent mist from the external surfaces of the article, which is conveyed by the conveyance means from the decontamination region, with clean gas.

2. The continuous decontamination device according to claim 1, wherein:

the mist control means includes one or more pairs of vibration boards, wherein the one or more pairs of vibration boards are arranged with board surfaces thereof being opposite each other from an outer peripheral side of the article conveyed in the conveyance direction by the conveyance means to concentrate the decontamination agent mist on the external surfaces of the article by directing a pressing force caused by the acoustic radiation pressure in a direction of the article conveyed inside the decontamination region.

3. The continuous decontamination device according to claim 2, wherein a vibration board, from the one or more pairs of vibrational boards, includes a base and a plurality of transmitters, and transmitters from the plurality of transmitters are spatially uniformly arranged on a planar surface of the base, and the transmitters are operated in phase with one another to generate a sound flow with a significantly directional ultrasound directed from a board surface of said vibration board in the vertical direction by mutually amplifying ultrasound outputs of the plurality of transmitters in a front direction and mutually canceling out said ultrasound outputs in a lateral direction.

4. The continuous decontamination device according to claim 3, configured to further reduce a size of the decontamination agent mist supplied to the inside of the decontamination region by ultrasonic vibration generated from the vibration board.

5. The continuous decontamination device according to claim 3, wherein:

the aeration region includes auxiliary vibration boards disposed adjacent to internal wall surfaces thereof, and the device is configured to ultrasonically vibrate the auxiliary vibration boards to generate sound flows from board surfaces by an ultrasound in the vertical direction to subject a condensed film of the decontamination agent mist that is residual on the external surfaces of the article conveyed inside the aeration region to ultrasonic vibration by said sound flows to promote the aeration efficiency.

6. The continuous decontamination device according to claim 3, wherein:

the conveyance means is (6*a*) a conveyor device dimensioned to have the article placed on a bottom wall surface thereof and to convey said article as a roller conveyor and a mesh conveyor, or (6*b*) a support device configured to support a side surface portion of the article and to convey the article as a timing belt.

7. The continuous decontamination device according to claim 3, wherein:

the article to be decontaminated is configured to accommodate medical appliances including a sterile syringe or a vial.

* * * * *